United States Patent
Pugh

(10) Patent No.: US 9,901,322 B2
(45) Date of Patent: Feb. 27, 2018

(54) OPHTHALMIC LENS WITH RETINAL VASCULARIZATION MONITORING SYSTEM

(71) Applicant: Johnson & Johnson Vision Care, Inc., Jacksonville, FL (US)

(72) Inventor: Randall Braxton Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/471,435

(22) Filed: Mar. 28, 2017

(65) Prior Publication Data

US 2017/0238900 A1 Aug. 24, 2017

Related U.S. Application Data

(62) Division of application No. 14/087,315, filed on Nov. 22, 2013, now Pat. No. 9,642,525.

(51) Int. Cl.
*A61B 8/10* (2006.01)
*G02C 7/04* (2006.01)
(Continued)

(52) U.S. Cl.
CPC .............. *A61B 8/10* (2013.01); *A61B 3/1241* (2013.01); *A61B 3/14* (2013.01); *A61B 5/004* (2013.01);
(Continued)

(58) Field of Classification Search
CPC ........... A61B 8/10; A61B 3/1241; A61B 3/14; A61B 8/02; A61B 8/5223; A61F 2/1451;
(Continued)

(56) References Cited

U.S. PATENT DOCUMENTS 5,261,407 A 11/1993 Nishigaki
6,213,943 B1 4/2001 Abreu
(Continued)

FOREIGN PATENT DOCUMENTS

GB 2464981 A 5/2010
RU 2379727 C1 1/2010
(Continued)

OTHER PUBLICATIONS

Safar M.E. et al., Pulsed Doppler: Diameter, Blood Flow Velocity and Volumic Flow of the Brachial Artery in Sustained Essential Hypertension, *Circulation*, Feb. 1, 1981, vol. 63, No. 2, pp. 393-400.

*Primary Examiner* — Bo J Peng

(57) ABSTRACT

The present invention discloses an ophthalmic device with a retinal vascularization monitoring system and associated methods. In some embodiments, the ophthalmic device can be a contact lens with a retinal vascularization monitoring system that can be used to monitor temporal changes of a pulsating vessel forming part of the retinal vascularization. Further, the retinal vascularization monitoring system may include elements for delivering a signal, including an audible and/or visual message, to the user that can be useful for identifying abnormal conditions such as a cardiac failure without delay. The audible and/or visual messages can be signals communicated to the user using one or both of the ophthalmic device and a wireless device in communication with the ophthalmic device.

11 Claims, 8 Drawing Sheets

(51) Int. Cl.
 *A61B 3/14* (2006.01)
 *A61B 5/00* (2006.01)
 *A61F 9/00* (2006.01)
 *A61B 8/02* (2006.01)
 *A61B 8/08* (2006.01)
 *A61F 2/14* (2006.01)
 *A61B 3/12* (2006.01)
 *A61F 2/16* (2006.01)
 *G02C 11/00* (2006.01)
 *A61B 8/00* (2006.01)

(52) U.S. Cl.
 CPC .............. *A61B 8/02* (2013.01); *A61B 8/5223* (2013.01); *A61F 2/1451* (2015.04); *A61F 2/16* (2013.01); *A61F 9/0017* (2013.01); *G02C 7/04* (2013.01); *G02C 11/10* (2013.01); *A61B 8/42* (2013.01); *A61B 8/4483* (2013.01)

(58) Field of Classification Search
 CPC ......... A61F 2/16; A61F 9/0017; G02C 11/10; G02C 7/04
 See application file for complete search history.

(56) References Cited

U.S. PATENT DOCUMENTS

| | | | |
|---|---|---|---|
| 2003/0069489 A1* | 4/2003 | Abreu | A61B 3/1241 600/405 |
| 2005/0197571 A1 | 9/2005 | McVeigh | |
| 2012/0212696 A1 | 8/2012 | Trajkovska | |
| 2013/0046179 A1* | 2/2013 | Humayun | A61B 8/10 600/440 |

FOREIGN PATENT DOCUMENTS

| | | |
|---|---|---|
| WO | WO2000025662 A1 | 5/2000 |
| WO | WO2008091859 A1 | 7/2008 |
| WO | WO2009100439 A2 | 8/2009 |
| WO | WO2010051225 A1 | 5/2010 |
| WO | WO2010102310 A2 | 9/2010 |
| WO | WO2010107930 A1 | 9/2010 |

* cited by examiner

OPHTHALMIC LENS WITH RETINAL VASCULARIZATION MONITORING SYSTEM

CROSS REFERENCE TO RELATED APPLICATION

The present application is a divisional application of U.S. patent application Ser. No. 14/087,315 filed on Nov. 22, 2013.

FIELD OF THE INVENTION

This invention describes an energized Ophthalmic Device with a retinal vascularization monitoring system, and more specifically, the system used for the early detection of abnormal cardiac related conditions of a user.

BACKGROUND OF THE INVENTION

Traditionally, an ophthalmic device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. An ophthalmic device has traditionally been a passive device.

Novel ophthalmic devices based on energized ophthalmic inserts have recently been described. These devices may use the energization function to power active optical components. For example, a wearable lens may incorporate a lens assembly having an electronically adjustable focus to augment or enhance performance of the eye, and/or embeddable microelectronic devices that can be useful for the diagnosis and treatment of various health conditions or diseases.

Retinal vascular imaging has recently been explored as a non-invasive alternative tool to analyze the role and pathophysiology of the microvasculature. For instance, research has demonstrated that a correlation exists between conditions of the retinal vascularization, forming part of the microvasculature, and cardiovascular disease and hypertension. Typically, screening for the diagnosis and monitoring of cardiac conditions is done by an Electrocardiogram (also known as a ECG or EKG). An electrocardiogram can be used to measure the rate and regularity of heartbeats, the size and position of the chambers, the presence of any damage to the heart, and the effects of drugs or devices used to regulate the heart by analysis of the electrical activity of the heart over a period of time, as detected by electrodes attached to the surface of the skin and recorded by a device external to the body. However, getting an electrocardiogram for many patients can not only be highly burdensome but is also not recommended for individuals absent additional symptoms or for patients who are at low risk. Moreover, for those at higher risk electrocardiogram screening results can be inconclusive.

The microvasculature includes vessels between 100 µm and 300 µm making the study and analysis of these vessels difficult in part due to their size. In addition, until recently the methods and procedures used to investigate the microvasculature have all been invasive and require highly specialized tools and settings. More recently however, with advances in photographic image techniques and computer-assisted image analysis techniques, alternative techniques that utilize non-invasive large complex cameras have been explored. These non-invasive techniques in turn can allow physicians and researchers to image and study the retinal vascularization of a patient.

Although these new non-invasive techniques can be useful for the study and understanding of microvascular changes, they continue to require specialized equipment and settings for the imaging of the retinal vascularization of a patient. Consequently, the timing and changes that can be observed are interrupted by large periods of time (i.e. time between appointments), and therefore less than optimal. In order to overcome the aforementioned limitations and improve the accuracy of the retinal vascularization analysis, novel and reliable systems/methods that can monitor changes in the retinal vascularization of a patient innocuously and without significant delay are desired.

SUMMARY OF THE INVENTION

The foregoing needs are met, to a great extent, by the present invention, wherein in one aspect an Energized Ophthalmic Device incorporating a Retinal Vascularization Monitoring System is disclosed. The Retinal Vascularization Monitoring System can include a micro-piezoelectric element with a feedback circuit that can be used for the ultrasound imaging of at least a portion of the retinal microvascularization. The image captured can be analyzed to measure and quantify changes without significant delay. The changes can be used to signal, to the patient or physician, or record abnormal cardiac pulse of a patient. In some embodiments, alternatively or in addition to the imaging aspect of the Retinal Vascularization Monitoring System, a microsensor can be used to capture signals arising from a person's cardiac pulse.

According to some aspects of the disclosure, an Energized Ophthalmic Device with a Retinal Vascularization Monitoring System is disclosed. The Ophthalmic Device including: a Media Insert comprising a front curve arcuate surface and a back curve arcuate surface, wherein the front curve arcuate surface and the back curve arcuate surface form a cavity capable of containing an Energy Source dimensioned to conform to an area within the cavity, wherein the Energy Source is in electrical connection and capable of Energizing a micro-piezoelectric element with an electronic feedback circuit and a controller, the controller comprising a computer processor in digital communication with a digital media storage device and wherein the digital media storage device stores software code; a transmitter in logical communication with the processor and also in logical communication with a communication network, wherein the software is executable upon demand and operative with the processor to: receive data descriptive of at least one identified portion of a pulsating vessel forming part of a retinal vascularization of an eye; cause the micro-piezoelectric element to output a signal towards the at least one identified portion of the pulsating vessel; receive data from the electronic feedback circuit descriptive of the change of the outputted signal outputted towards the at least one identified portion of the pulsating vessel; image the at least one identified portion of the pulsating vessel using the data received from the electronic feedback circuit; and monitor changes of the retinal vascularization by comparing said at least one identified portion imaged with a previous image over time.

In additional aspects of the disclosure, an associated method of monitoring the retinal vascularization of a patient's eye is disclosed. The method including: identifying at least one location of a pulsating vessel in the retinal vascularization of an eye; providing an ophthalmic device with a Retinal Vascularization Monitoring System comprising an Energy Source in electrical connection and capable of Energizing a micro-piezoelectric element with an electronic feedback circuit and a controller comprising a computer processor, a digital media storage device, a transmitter in logical communication with the processor and also in logical communication with a communication network; outputting a signal towards the at least one pulsating location identified using the micro-piezoelectric element with the electronic feedback circuit; receiving, using the feedback circuit, a return signal from the outputted signal; imaging the at least one pulsating location using the change in the outputted signal and the return signal; and monitoring changes of the retinal vascularization by comparing said at least one identified portion images with a previous image of the same said at least one identified portion over time.

In yet additional aspects of the disclosure, the method of monitoring the retinal vascularization of a patient's eye can alternatively include: identifying locations forming part of the retinal vascularization of the patient's eye including at least a portion of a pulsating vessel; providing an ophthalmic device with a Retinal Vascularization Monitoring System comprising an Energy Source in electrical connection and capable of Energizing a micro-piezoelectric element with an electronic feedback circuit and a controller comprising a computer processor, a digital media storage device, a transmitter in logical communication with the processor and also in logical communication with a communication network; detecting a change in a controlled signal outputted towards the at least said portion of the pulsating vessel identified; imaging the at least said portion of the retinal vascularization of the patient's eye using the detected change in said controlled signal; and recording the changes in the at least said portion of the retinal vascularization between a series of images over time.

There has thus been outlined, rather broadly, certain aspects of the invention in order that the detailed description thereof herein may be better understood, and in order that the present contribution to the art may be better appreciated. There are, of course, additional aspects of the invention that will be described below and which will form the subject matter of the claims appended hereto.

In this respect, before explaining at least one aspect of the invention in detail, it is to be understood that the invention is not limited in its application to the details of construction and to the arrangements of the components set forth in the following description or illustrated in the drawings. The invention is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the invention. It is important, therefore, that the claims be regarded as including such equivalent constructions insofar as they do not depart from the spirit and scope of the invention.

BRIEF DESCRIPTION OF THE DRAWINGS

The foregoing and other features and advantages of the invention will be apparent from the following, more particular description of exemplary embodiments of the invention, as illustrated in the accompanying drawings.

DETAILED DESCRIPTION OF THE INVENTION

Figure 1A:
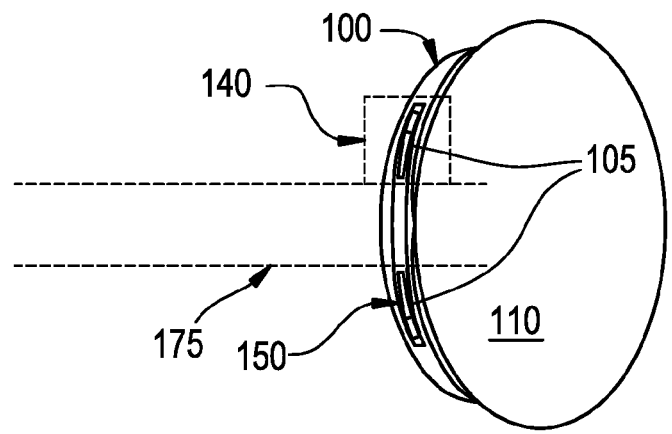
FIG. 1A is a diagrammatic cross section representation of a first exemplary energized ophthalmic device comprising both optics and a retinal vascularization monitoring system in accordance with aspects of the present disclosure.

The disclosure will now be described with reference to the drawing figures, in which like reference numerals refer to like parts throughout.

Various aspects of the ophthalmic device disclosed may be illustrated by describing components that are coupled, sealed, attached, and/or joined together. As used herein, the terms "coupled", "sealed", "attached", and/or "joined" are used to indicate either a direct connection between two components or, where appropriate, an indirect connection to one another through intervening or intermediate components. In contrast, when a component is referred to as being "directly coupled", "directly sealed", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations in addition to the orientation depicted in the drawings. By way of example, if aspects of an exemplary ophthalmic device shown in the drawings are turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an Ophthalmic Device with a Retinal Vascularization Monitoring System may be illustrated with reference to one or more exemplary embodiments. As used herein, the term "exemplary" means "serving as an example, instance, or illustration," and should not necessarily be construed as preferred or advantageous over other embodiments disclosed herein.

Glossary

In this description and claims directed to the disclosed invention, various terms may be used for which the following definitions will apply:

Energized: as used herein refers to the state of being able to supply electrical current to or to have electrical energy stored within.

Energy: as used herein refers to the capacity of a physical system to do work. Many uses within this disclosure may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Ophthalmic Device: as used herein refers to any device that resides in or on the eye. These devices may provide optical correction, may be cosmetic, or may provide functionality unrelated to vision. For example, the term Ophthalmic Lens may refer to a contact lens, intraocular lens, overlay lens, ocular insert, optical insert, or other similar device through which vision can be corrected or modified, detection and treatment of a condition or through which eye physiology is cosmetically enhanced (e.g. iris color) without impeding vision. In addition to or alternatively, the Ophthalmic Lens may provide non-optic functions such as, for example, monitoring glucose levels, cardiac rhythm, recording a measurement, delivering sound signals, delivering visual signals, and/or administrating medicine. In some embodiments, the preferred lenses of the invention are soft contact lenses are made from silicone elastomers or hydrogels, which include, for example, silicone hydrogels, and fluorohydrogels.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an insert that that can form part of an Energized Ophthalmic Device. The Energization Elements and circuitry may be incorporated in the Media Insert. The Media Insert can define the primary purpose of the Energized Ophthalmic Device. For example, in embodiments where the Energized Ophthalmic Device allows the user to adjust the optic power, the Media Insert may include Energization Elements that control a liquid meniscus portion in the Optical Zone of the Ophthalmic Device. Alternatively, a Media Insert may be annular so that the Optical Zone is void of material. In such embodiments, the Energized function of the Lens may not be optic quality but may be, for example, monitoring glucose, sound/light delivery, and/or administering medicine.

Micro-Acoustic Element(s): as used herein can refer to a micro acoustic electromechanical system and/or related components that can be used to conduct audible frequencies from the orb of the eye to the inner ear through the bones in the skull. In some embodiments, the micro-acoustic elements can include, for example, a micro-electromechanical (MEMS) piezoelectric acoustic transducer and/or a condenser acoustic device, Energized by an Energy Source contained in the Ophthalmic Device.

Operating Mode: as used herein refers to a high current draw state where the current over a circuit allows the device to perform its primary Energized function.

Optical Zone: as used herein refers to an area of an Ophthalmic Device through which a wearer of the Ophthalmic Device sees.

Power: as used herein refers to work done or energy transferred per unit of time.

Reenergize or Recharge: as used herein refers to restoring to a state with higher capacity to do work. Many uses within this invention may relate to restoring a device to the capability to flow electrical current at a certain rate and for a certain reestablished period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Retinal Vascularization Monitoring System: as used herein refers an Energized micro-piezoelectric element with a feedback circuit that can be configured to be included in an ophthalmic device and enable the visualization and detection a pulsating vessel forming part of the retinal microvascularization. In some embodiments, the retinal vascularization monitoring system may focus on imaging one or more pre-identified specific areas of the retina in which changes of the vessels can be observed due to cardiac rhythm or an abnormal condition. In addition or alternatively, the retinal vascularization monitoring system can include a microsensor that can be used to capture/hear frequency signals arising from a person's cardiac pulse.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an Ophthalmic Device. In some embodiments, the Substrate Insert also supports one or more functional electrical or electromecanical components.

Switching Mechanism: as used herein refers to a component integrated with the circuit providing various levels of resistance that may be responsive to an outside stimulus, which is independent of the Ophthalmic Device.

Recent developments in Ophthalmic Devices including, for example, contact lenses, have occurred enabling Functionalized Ophthalmic Devices that can be Energized. The Energized Ophthalmic Device can comprise the necessary elements to correct and/or enhance the vision of users using embedded micro-electronics. Additional functionality using micro-electronics can include, for example, variable vision correction, tear fluid analysis, audio, and/or visual feedback to the user. In addition to having the capability of providing vision correction functionality, the present disclosure provides for an Ophthalmic Device that includes a Retinal Vascularization Monitoring System. The Retinal Vascularization Monitoring System can include an Energized micro-piezoelectric element with a feedback circuit. In some embodiments, the Ophthalmic Device can be in wireless communication with one or more wireless device(s) and transmit signal data that can be used for the determination of an abnormal condition and a correlated cause and/or the cardiac rhythm of a user. The wireless device(s) can include, for example, a smart phone device, a tablet, a personal computer, a FOB, a drug pump, an MP3 player, a PDA, and the such.

In some aspects of the present disclosure, an Ophthalmic Device can include a Retinal Vascularization Monitoring System to enable the visualization and detection of pulses of vessels forming part of the retinal microvascularization. In some embodiments, the Retinal Vascularization Monitoring System may focus on imaging one or more specific areas of the retina in which greater changes of the vessels can be observed due to cardiac rhythm or an abnormal pre-identified condition. In addition or alternatively, the Retinal Vascularization Monitoring System can include a microsensor that can be used to capture/hear frequency signals arising from a person's cardiac pulse.

Referring now to FIG. 1A, a diagrammatic cross section representation of a first exemplary Energized Ophthalmic Device 100 comprising both optics and a Retinal Vascularization Monitoring System is depicted. According to some aspects of the present disclosure, the Ophthalmic Device 100 of the present disclosure may be a contact lens resting on the anterior surface of a patent's eye 110. The contact lens may be a soft hydrogel lens and can include a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Embedded by the hydrogel portion partially or entirely, or in some embodiments placed onto the hydrogel portion, can be a Functionalized Media Insert 150. The Media Insert 150 can be used to encapsulate Functionalized elements 105, including electronic and electromecanical elements, and in some embodiments one or more Energy Source (in section 140 magnified in FIG. 1B). In some embodiments, the Functionalized elements 105 can preferably be located outside of the Optical Zone 175, such that the device does not interfere with the patient's sight. Functionalized elements 105 may be powered through an external means, energy harvesters, and/or Energization elements contained in the Ophthalmic Device 100. For example, in some embodiments the power may be received using an antenna receiving RF signals that is in communication with the electronic elements 105.

Figure 1B:
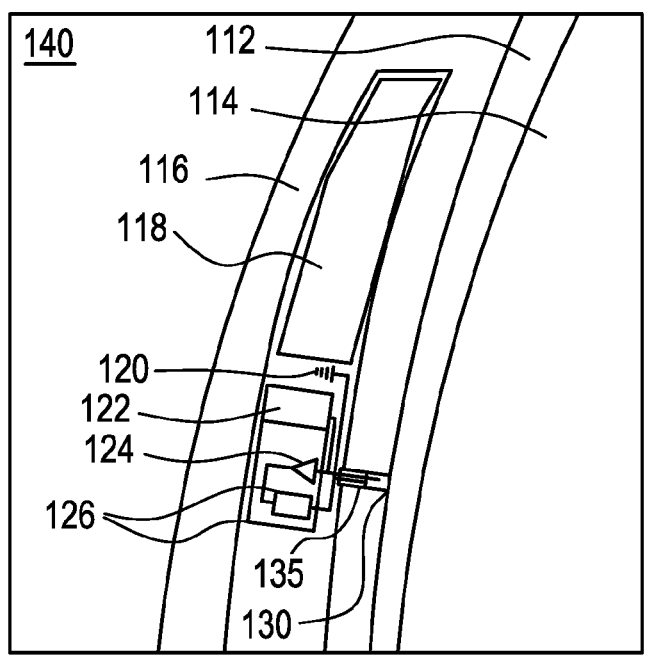
FIG. 1B is an enlarged portion of the cross section depicted in FIG. 1A showing aspects of the retinal vascularization monitoring system in accordance with aspects of the present disclosure.

Referring now to FIG. 1B, an enlarged portion 140 of the cross section depicted in FIG. 1A showing aspects of the Retinal Vascularization Monitoring System is depicted. In particular, the enlarged portion 140 illustrates a hydrogel portion 116 of the Ophthalmic Device 100 resting on Ocular fluid 112 on the anterior surface of the eye 110. Ocular fluid 112 can include any one, or a combination of: tear fluid, aqueous humour, vitreous humour, and other interstitial fluids located in the eye. The hydrogel portion 116 may encapsulate the Media Insert 150 which in some embodiments can include Energization elements 118, such as a battery and a load, along with components of the Retinal Vascularization Monitoring System 126.

The Retinal Vascularization Monitoring System 126 can include a wireless Communication element 120, such as a RF antenna in connection with a controller 122. The controller 122 can be used to control a piezoelectric transducer 130, a pick up 135, and an electronic feedback circuit including an amplifier 124 and a band-pass filter 126 which can all be powered through the Energization elements 118 contained within the Media Insert 150. The piezoelectric transducer 130 and the pick-up 135 can resonate a signal and measure the change in the return signal to image one or more portions of the Retinal Vascularization. The piezo-electric transducer may be placed in contact with the retina. Upon the application of electrical pulses, ultrasound pulses emanate from it for them to echo back to the surface and converted back to electrical pulses that can then be processed by the system and formed into an image. The images can be produced by surfaces or boundaries between two different types of tissues, such as the vessels forming part of the retina and the vitreous humour of the eye. Because the vitreous humour is a relatively homogenous gelatinous mass with insignificant amounts of solid matter, an identified portion of the retinal vascularization may be imaged by changing the focal depth from the transducer. The focal depth can be adjusted by changing the time delay between the electrical pulses. By sending ultrasound pulses at different depths around an identified pulsating vessel, the imaging definition required to identify small temporal changes in width and displacement can be achieved.

Figure 2A:
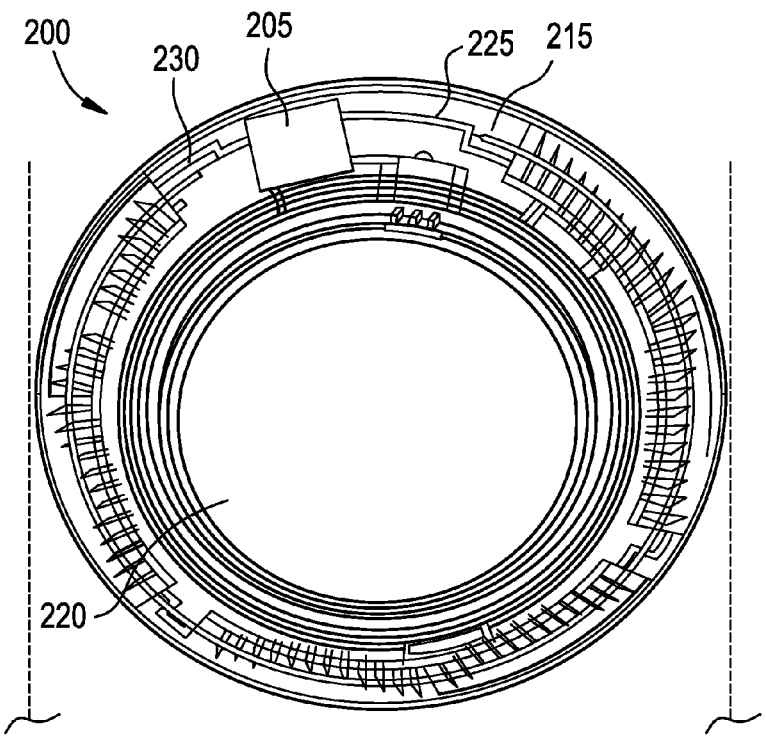
FIG. 2A is a diagrammatic representation of the top view of a media insert that may be included as part of an ophthalmic device comprising both optics and the retinal vascularization monitoring system in accordance with aspects of the present disclosure.

Referring now to FIG. 2A, a diagrammatic representation of the top view of a Media Insert 200 that may be included as part of another exemplary Ophthalmic Device 100 comprising both optics and the Retinal Vascularization Monitoring System 205 is depicted. In particular, a top view of an exemplary Media Insert 200 for an Energized Ophthalmic Device 250 (shown in FIG. 2B) that can include Retinal Vascularization Monitoring System 205 is illustrated. The Media Insert 200 may comprise an Optical Zone 220 that may or may not be functional to provide vision correction. Where the energized function of the ophthalmic device is unrelated to vision, the Optic Zone 220 of the Media Insert 200 may be void of material. In some embodiments, the Media Insert 200 may include a portion not in the Optical Zone 220 comprising a substrate 215 incorporated with energization elements 210 and electronic components 205 which include Retinal Vascularization Monitoring System elements.

In some embodiments, a power source 210, which may be, for example, a battery, and a load 205, which may be, for example, a semiconductor die, may be attached to the substrate 215. Conductive traces 225 and 230 may electrically interconnect the electronic components 205 and the energization elements 210. In some embodiments, the Media Insert 200 can be fully encapsulated to protect and contain the energization elements 210, traces 225 and 230, and electronic components 205. In some embodiments, the encapsulating material may be semi-permeable, for example, to prevent specific substances, such as water, from entering the Media Insert 200 and to allow specific substances, such as ambient gasses, fluid samples, and/or the byproducts of reactions within Energization Elements 210, to penetrate and/or escape from the Media Insert 200.

Figure 2B:
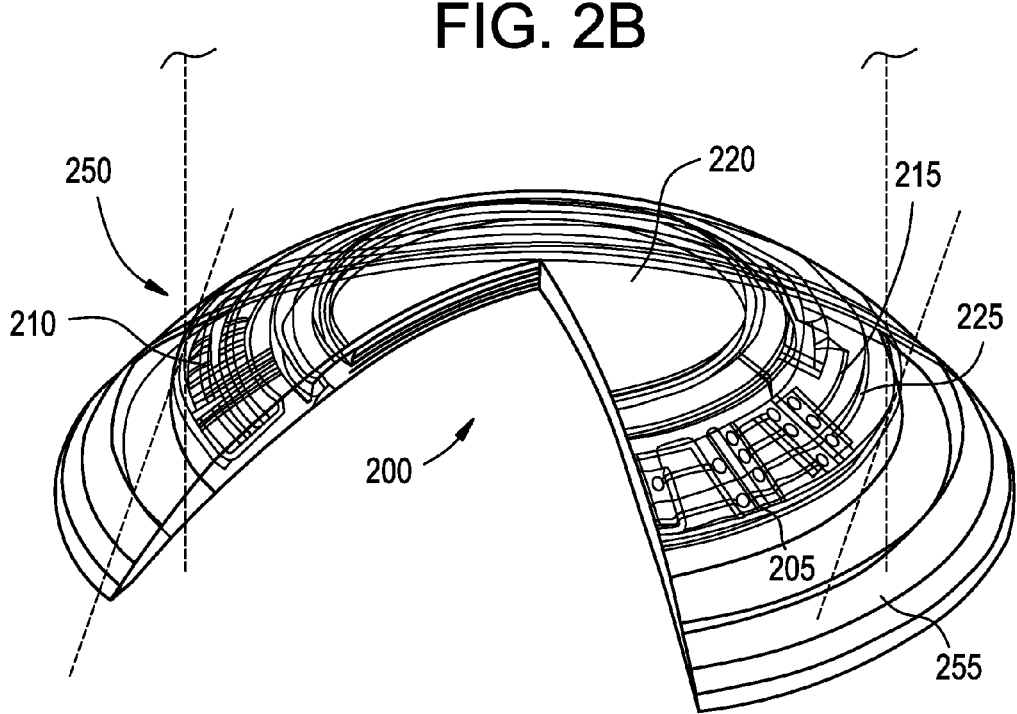
FIG. 2B is a diagrammatic representation of an isometric view of an ophthalmic device including the media insert depicted in FIG. 2A comprising the retinal vascularization monitoring system in accordance with aspects of the present disclosure.

Referring now to FIG. 2B, a diagrammatic representation of an isometric view of an ophthalmic device including the Media Insert depicted in FIG. 2A comprising both optics and the Retinal Vascularization Monitoring System is depicted. The Media Insert 200 may be included in/or on an Ophthalmic Device 250, which may also comprise a polymeric biocompatible material. The Ophthalmic Device 250 may include a rigid center, soft skirt design wherein a central rigid optical element comprises the Media Insert 200. In some specific embodiments, the Media Insert 200 may be in direct contact with the atmosphere and/or the corneal surface on respective anterior and posterior surfaces, or alternatively, the Media Insert 200 may be encapsulated in the Ophthalmic Device 250. The periphery 255 of the Ophthalmic Device 250 may be a soft skirt material, including, for example, a hydrogel material. The infrastructure of the Media Insert 200 and the Ophthalmic Device 250 can provide an environment to monitor the retinal microvascularization according to aspects of the present invention. In addition, in the present exemplary Ophthalmic Device 250, Micro-Acoustic Elements may be placed insider or on a surface of the media insert 200 to transmit audible signals through bone resonance through the skull and to the cochlea. In some embodiments, the audible signals transmitted to the user using the Micro-Acoustic Elements may be transmitted, for example, when the cardiac rhythm is determined to be outside a predetermined threshold based on monitored changes of the retinal vascularization. For example, the audible signal may be a recommended action and/or warning based on cardiac rhythm or an abnormal condition.

Figure 3:
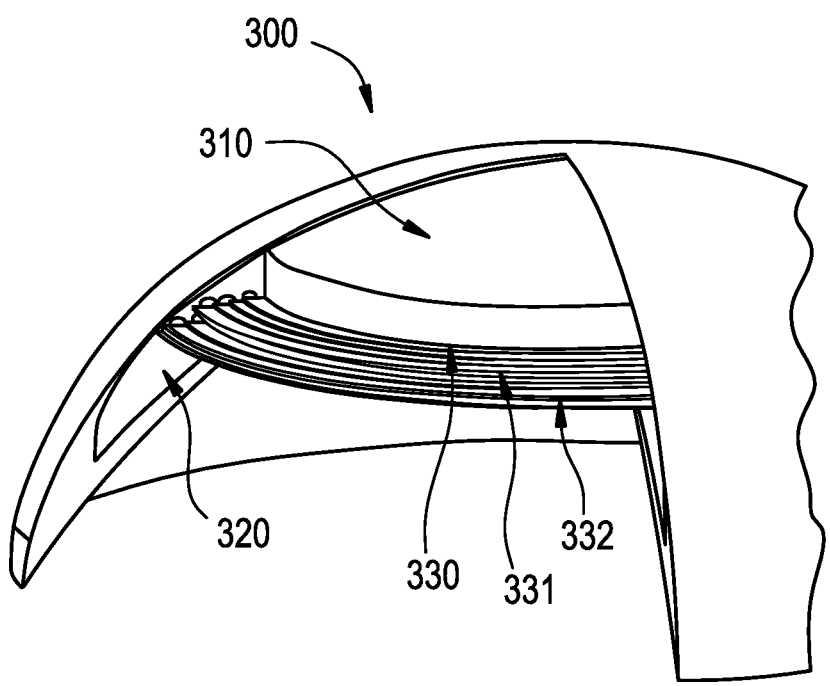
FIG. 3 is a diagrammatic sectioned isometric view of another exemplary energized ophthalmic device comprising both optics and the retinal vascularization monitoring system in accordance with aspects of the present disclosure.

Referring now to FIG. 3, a diagrammatic representation of another exemplary energized Ophthalmic Device comprising both optics and the Retinal Vascularization Monitoring System is depicted. In particular, a three dimensional cross section representation of an exemplary Ophthalmic Device 300 including a Functionalized Layer Media Insert 320 configured to include the Retinal Vascularization Monitoring System on one or more of its layers 330, 331, 332 is illustrated. In the present exemplary embodiment, the Media Insert 320 can surround the entire periphery of the Ophthalmic Device 300. One skilled in the art can understand that the actual Media Insert 320 may comprise a full annular ring or other shapes that still may reside inside or on the hydrogel portion of the Ophthalmic Device 300 and be within the size and geometry constraints presented by the ophthalmic environment of the user.

Layers 330, 331 and 332 are meant to illustrate three of numerous layers that may be found in a Media Insert 320 formed as a stack of functional layers. In some embodiments, for example, a single layer may include one or more of: active and passive components and portions with structural, electrical or physical properties conducive to a particular purpose including the Communication System functions described in the present disclosure. Furthermore, in some embodiments, a layer 330 may include an Energy Source, such as, one or more of: a battery, a capacitor and a receiver within the layer 330. Item 331 then, in a non-limiting exemplary sense may comprise microcircuitry in a layer that detects actuation signals for the Ophthalmic Device 300. In some embodiments, a power regulation layer 332, may be included that is capable of receiving power from external sources, charges the battery layer 330 and controls the use of battery power from layer 330 when the Ophthalmic Device 300 is not in a charging environment. The power regulation may also control signals to an exemplary active lens, demonstrated as item 310 in the center annular cutout of the Media Insert 320.

An Energized Ophthalmic Device 300 with an embedded Media Insert 320 may include an Energy Source, such as an electrochemical cell or battery (lithium ion cell) as the storage means for the energy and in some embodiments, encapsulation, and isolation of the materials comprising the energy source from an environment into which an Ophthalmic Device 300 is placed. In some embodiments, a Media Insert 320 can also include a pattern of circuitry, components, and Energy Sources. Various embodiments may include the Media Insert 320 locating the pattern of circuitry, components and Energy Sources around a periphery of an Optic Zone through which a wearer of an Ophthalmic Lens would see, while other embodiments may include a pattern of circuitry, components and Energy Sources which are small enough to not adversely affect the sight of the Ophthalmic Lens wearer and therefore the Media Insert 320 may locate them within, or exterior to, an Optical Zone without consequence.

Reference has been made to electronic circuits making up part of the componentry of Ophthalmic Devices incorporating a Retinal Vascularization Monitoring System. In some embodiments according to aspects of the disclosure, a single and/or multiple discrete electronic devices may be included as discrete chips, for example, in the ophthalmic Media Inserts. In other embodiments, the energized electronic elements can be included in the Media Insert in the form of Stacked Integrated Components. Accordingly and referring now to FIG. 4, a schematic diagram of an exemplary cross section of a stacked die integrated components implementing the Retinal Vascularization Monitoring System 410 is depicted. In particular, the Media Insert may include numerous layers of different types which are encapsulated into contours consistent with the ophthalmic environment that they will occupy. In some embodiments, these Media Inserts with Stacked Integrated Component layers may assume the entire annular shape of the Media Insert. Alternatively in some cases, the Media Insert may be an annulus whereas the Stacked Integrated Components may occupy just a portion of the volume within the entire shape.

Figure 4:
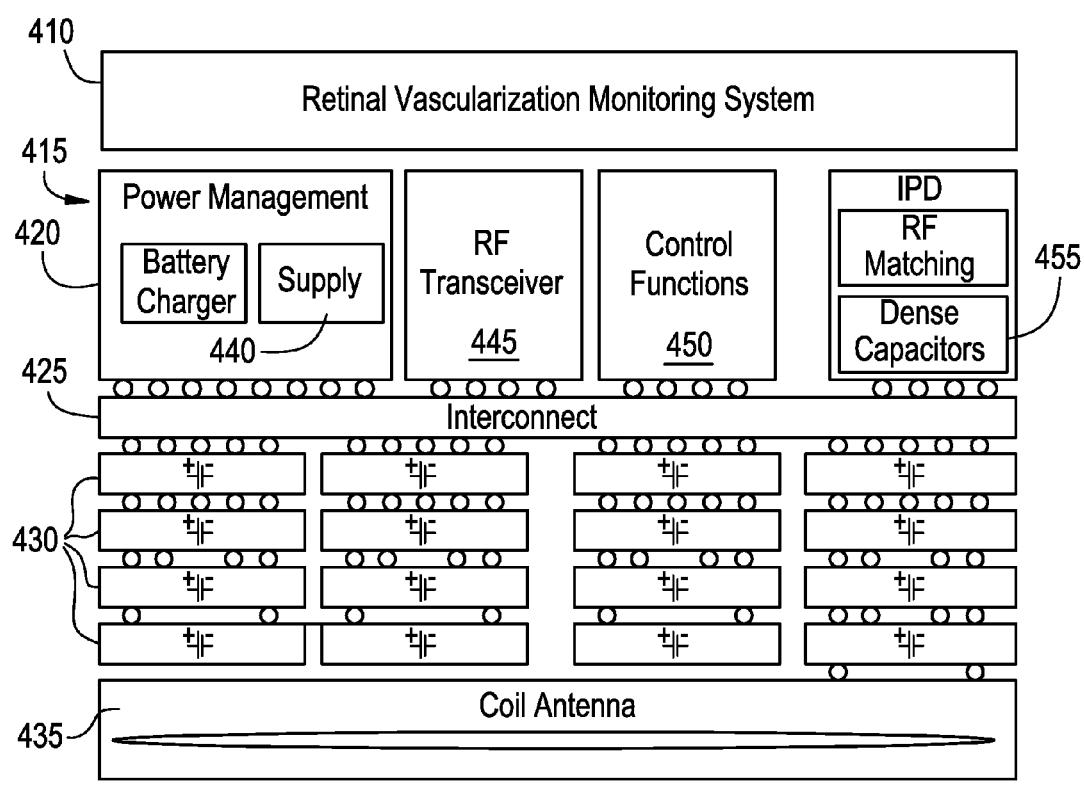
FIG. 4 is a schematic diagram of an exemplary cross section of a stacked die integrated components implementing the retinal vascularization monitoring system in accordance with aspects of the present disclosure.

As shown in FIG. 4, there may be thin film batteries 430 used to provide energization. In some embodiments, these thin film batteries 430 may comprise one or more of the layers that can be stacked upon each other with multiple components in the layers and interconnections therebetween.

In some embodiments, there may be additional interconnections between two layers that are stacked upon each other. In the state of the art there may be numerous manners to make these interconnections; however, as demonstrated the interconnection may be made through solder ball interconnections between the layers. In some embodiments only these connections may be required; however, in other cases the solder balls may contact other interconnection elements, as for example with a component having through layer vias.

In other layers of the Stacked Integrated Component Media Insert, a layer 425 may be dedicated for the interconnections two or more of the various components in the interconnect layers. The interconnect layer 425 may contain, vias and routing lines that can pass signals from various components to others. For example, interconnect layer 425 may provide the various battery elements connections to a power management unit 420 that may be present in a technology layer 415. Other components in the technology layer 415 can include, for example, a transceiver 445, control components 450 and the like. In addition, the interconnect layer 425 may function to make connections between components in the technology layer 415 as well as components outside the technology layer 415; as may exist for example in the integrated passive device 455. There may be numerous manners for routing of electrical signals that may be supported by the presence of dedicated interconnect layers such as interconnect layer 425.

In some embodiments, the technology layer 415, like other layer components, may be included as multiple layers as these features represent a diversity of technology options that may be included in Media Inserts. In some embodiments, one of the layers may include CMOS, BiCMOS, Bipolar, or memory based technologies whereas the other layer may include a different technology. Alternatively, the two layers may represent different technology families within a same overall family; as for example one layer may include electronic elements produced using a 0.5 micron CMOS technology and another layer may include elements produced using a 20 nanometer CMOS technology. It may be apparent that many other combinations of various electronic technology types would be consistent within the art described herein.

In some embodiments, the Media Insert may include locations for electrical interconnections to components outside the insert. In other examples, however, the Media Insert may also include an interconnection to external components in a wireless manner. In such cases, the use of antennas in an antenna layer 435 may provide exemplary manners of wireless communication. In many cases, such an antenna layer 435 may be located, for example, on the top or bottom of the stacked integrated component device within the Media Insert.

In some of the embodiments discussed herein, the battery elements 430 may be included as elements in at least one of the stacked layers themselves. It may be noted as well that other embodiments may be possible where the battery elements 430 are located externally to the stacked integrated component layers. Still further diversity in embodiments may derive from the fact that a separate battery or other energization component may also exist within the Media Insert, or alternatively these separate energization components may also be located externally to the Media Insert.

Components of the Retinal Vascularization Monitoring System 410 may also be included in a Stacked Integrated Component architecture. In some embodiments, the Retinal Vascularization Monitoring System 410 components may be attached as a portion of a layer. In other embodiments, the entire Retinal Vascularization Monitoring System 410 may also comprise a similarly shaped component as the other Stacked Integrated Components.

Figure 5:
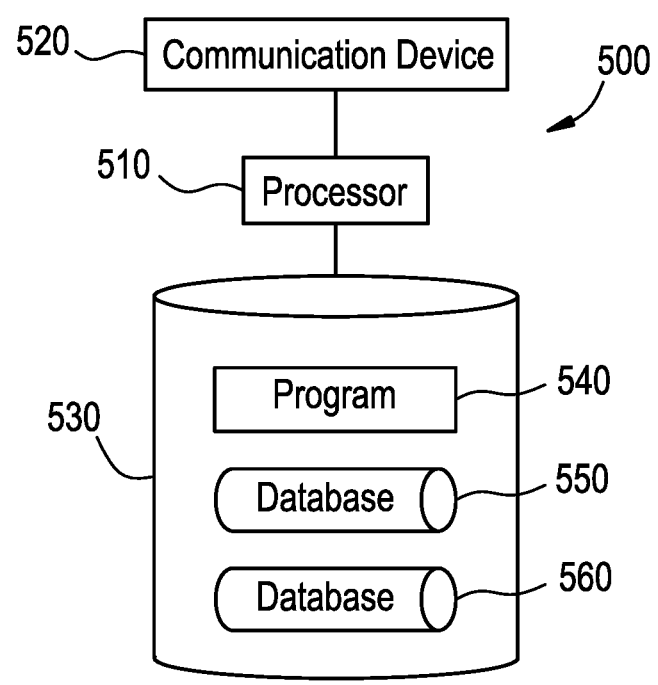
FIG. 5 is a schematic diagram of a processor that may be used to implement some aspects of the present disclosure.

Referring now to FIG. 5 is a schematic diagram of a processor that may be used to implement some aspects of the present disclosure is illustrated. The controller 500 can include one or more processors 510, which may include one or more processor components coupled to a communication device 520. In some embodiments, a controller 500 can be used to transmit energy to the Energy Source placed in the Ophthalmic Device.

The processors 510 can be coupled to a communication device configured to communicate energy via a communication channel. The communication device may be used to electronically communicate with components within the Media Insert, for example. The communication device 520 may also be used to communicate, for example, with one or more controller apparatus or programming/interface device components.

The processor 510 is also in communication with a storage device 530. The storage device 530 may comprise any appropriate information storage device, including combinations of magnetic storage devices, optical storage devices, and/or semiconductor memory devices such as Random Access Memory (RAM) devices and Read Only Memory (ROM) devices.

The storage device 530 can store a program 540 for controlling the processor 510. The processor 510 performs instructions of a software program 540, and thereby operates in accordance with the present invention. For example, the processor 510 may receive information descriptive of Media Insert placement, active target zones of the retinal vascularization, component placement, imaging resolution and/or frequency, and the like. The storage device 530 can also store other pre-determined ophthalmic related data in one or more databases 550 and 560. The database may include, for example, predetermined retinal zones exhibiting changes according to cardiac rhythm or an abnormal condition correlated with the retinal vascularization, measurement thresholds, metrology data, and specific control sequences for the system, flow of energy to and from a Media Insert, communication protocols, and the like. The database may also include parameters and controlling algorithms for the control of the Retinal Vascularization Monitoring System that may reside in the Ophthalmic Device as well as data and/or feedback that can result from their action. In some embodiments, that data may be ultimately communicated to/from an external reception wireless device.

Figure 6A:
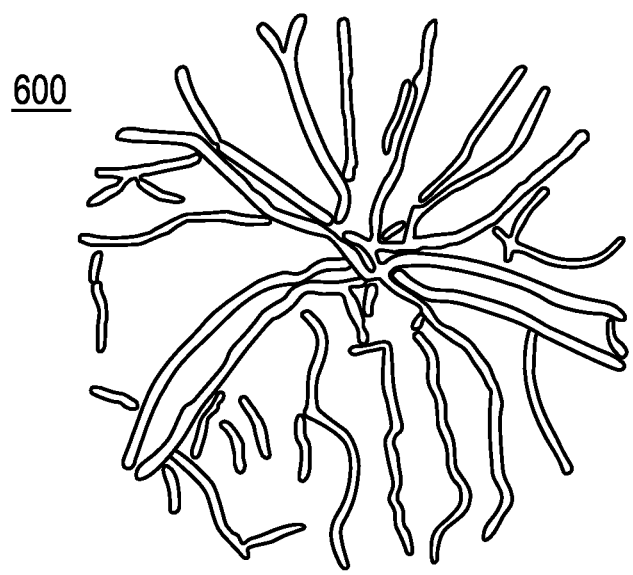
FIG. 6A illustrates a region of the retinal vascularization of an eye that can be utilized according to aspects of the present disclosure.

Referring now to FIG. 6A, a representation of a region of the retinal vascularization of an eye is depicted. In particular, a series of vessels forming part of the retinal vascularization 600 are shown as they would be viewed from the anterior portion of the eye by the ultrasound imaging system. In the present exemplary representation, the vessels branch off each other forming a dense pattern that can be useful to study the vessel tortuosity, the angle and number of bifurcations, and the length to width ratio. Monitoring temporal changes of the vessels or their overall structures can be useful to predict risk to cardiac conditions including, for example, microvascular disease or diabetes, and cardiac rhythm.

Figure 6B:
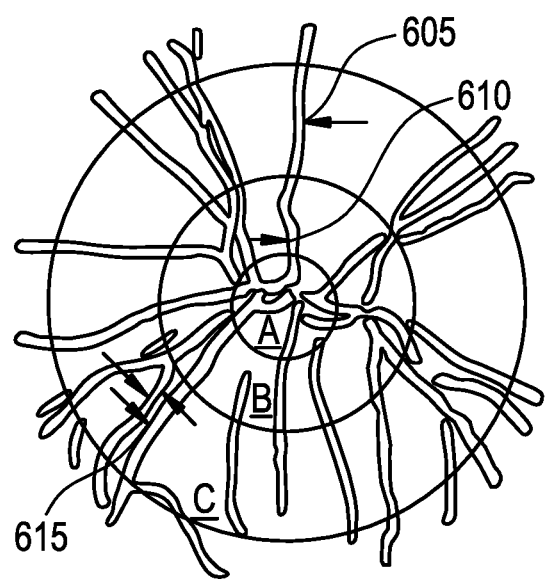
FIG. 6B illustrates the region of the retinal vascularization of an eye of FIG. 6A with a digital overlay that can be used for the analysis of the retinal vascularization according to aspects of the present disclosure.

Referring now to FIG. 6B, the region of the retinal vascularization of an eye of FIG. 6A is illustrated with a digital overlay useful for the analysis of changes of the retinal vascularization. In particular, the exemplary overlay can be useful to divide the observed region of the retinal vascularization into concentric grid sections that can be used for filtering and/or image segmentation. In some embodiments, grid sections may take other forms such including line patterns and the such. Concentric grid sections however may be preferred for filtering and image segmentation due to the arcuate shape of the cornea conforming to the spherical shape of the eye. When eye movement or flickering prevents processing of the different segmented portions, image processing techniques that include edge recognition can be used to connect the different segments allowing for the analysis of the portion of the retinal vascularization being monitored.

In the present example, changes of each vessel may be identified in relation to each of the particular concentric regions A, B, or C. By focusing the image analysis to a specific portion/region, the amount of image processing and analysis can be reduced thereby lowering power and processing requirements. For example, the frequency in which each of the regions is imaged can be alternated depending on the changes in pulse detected. In another scenario, only a first region that includes a segment of a pulsating vessel may be monitored until a change that falls outside a predetermined threshold is detected. Average changes in vessel diameter during the cardiac cycle may be approximately 1.2 μm for arteries and 1.6 μm for veins. Accordingly, a signal may be outputted once a change in diameter of an identified artery is less than 0.8 μm and greater than 1.6 μm over a short period of time. Similarly, a change in the diameter of a vein that is less than 1.2 μm or greater than 2.0 μm may trigger a signal. The signal may activate additional sensors, increase the rate of image capture, record the abnormality, and/or send a message to the user. The message can be sent to the user via an audio signal and/or a visual signal provided by the Ophthalmic Device itself or a device in wireless communication with the Ophthalmic Device.

Referring back to the present example shown in FIG. 6B, the width or diameter of a vessel may be monitored at point 605. Point 605 may have been identified as a positive pulsating point of reference during an initial retinal examination using high definition imaging technique including mydriatic and/or nonmydriatic retinal screenings. When an abnormal change in diameter or rate of pulsations is initially detected, point of reference 605 can be analyzed in conjunction with point of reference 610 pointing to the same vessel. Analysis at both points of reference may be used to provide the system with more measurements for the determination of blood pressure, for example. In some embodiments, other reference points on pulsating/non-pulsating vessels in a different region may also be monitored, simultaneously or in alternating modes, to ensure that the change is uniform throughout the vascularization. For example, at additional point of reference 615 in region C.

Figure 7:
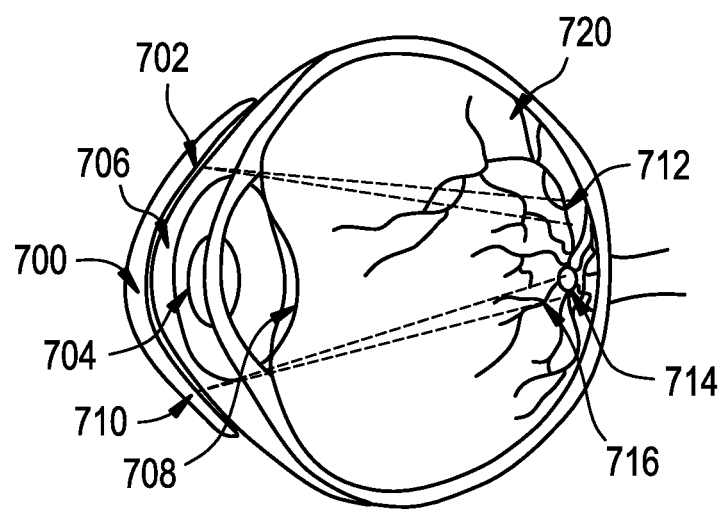
FIG. 7 illustrates a side cross section representation of a patient's eye with an Energized Ophthalmic Device according to aspects of the present disclosure.

Referring now to FIG. 7, a side cross section representation of a patient's eye with an exemplary Energized Ophthalmic Device is illustrated. In particular, an Ophthalmic Device 700 taking form of an Energized contact lens is illustrated resting on the cornea 706 with ocular fluid in at least some portions between the Ophthalmic Device 700 and the cornea 706. In some embodiments, the concave contour of the Ophthalmic Device 700 may be designed so that one or more piezoelectric transducers can rest directly on the cornea 706. Having the piezoelectric transducers resting directly on the cornea 706 can allow greater imaging detail as the ultrasonic pulses can travel directly towards the cornea 706 from focal points 702, 710. In alternative embodiments, only one or more than two focal points/piezoelectric transducers may be implemented. As depicted in the present exemplary embodiment, the piezoelectric transducer(s) are located on the periphery area of the Energized contact lens and outside of the line of sight to prevent vision interference. However, in alternative Energized contact lens devices the piezoelectric transducer may be located in the center region located in front of the pupil 704 also without significantly interfering with the vision of a user.

Accordingly, depending on the design of the Ophthalmic Device 700 the ultrasonic pulses may pass through the eye's lens 708 before passing through the vitreous humour 720 and reaching one or more retinal areas including pulsating vessels, e.g. 712 and 716. In some embodiments, the retinal areas may be pre-determined areas near or that include ocular parts serving a specific function or that can be used as a predictor of a particular condition including, for example, the macula 714 which may be screened for the early detection of peripheral vision loss.

Figure 8:
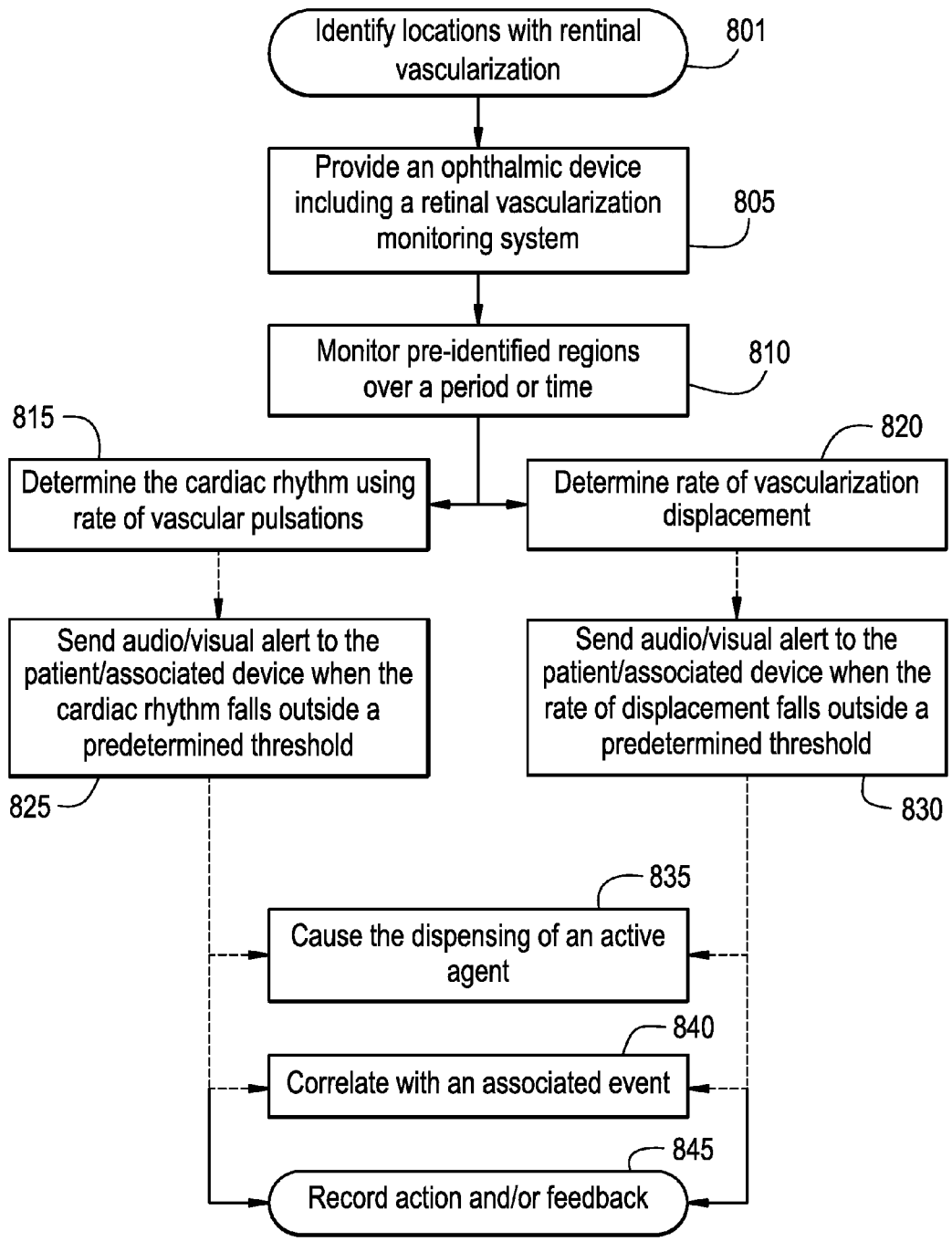
FIG. 8 illustrates method steps that can be implemented by the system according to aspects of the present disclosure.

Referring now to FIG. 8, method steps that can be implemented by the system according to aspects of the present disclosure are illustrated in a flowchart. Beginning at step 801, regions/zones with retinal vascularization can be identified for imaging. According to some aspects, the retinal vascularization in the identified region/zone includes portions of one or more pulsating vessels. These regions/zones can be identified using imaging systems that are capable of reproducing high definition images of the microvascularization in the retina. Imaging systems may include non-invasive OCT systems, or any other highly reliable mydriatic or nonmydriatic diagnostic imaging method used for geometrical measurements of retinal structures. Depth, shape, relative position, and structure of the vascularization may be pre-programmed into the Ophthalmic Device in order to lower processing/energy consumption requirements and reliably identify the target points in the areas monitored. In preferred embodiments, target points can be easily identifiable image features, such as, edges, crossing, or line boundaries of vessels.

At step 805, an Ophthalmic Device including a Retinal Vascularization Monitoring System is provided to a patient. In some embodiments, the Ophthalmic Device may include one or two Energized contact lenses configured to include a piezoelectric transducer with a feedback circuit used to provide an ultrasound pulse used to image the microvascularization of an eye. Said Energized contact lenses can additionally be capable of providing other functions including providing vision correction and/or enhancement via physical characteristics, wireless communication with other devices, and emitting visual and/or auditory signals to the user. The design of the Ophthalmic Device and, in particular, the location of the piezo-electric transducer forming part of the Retinal Vascularization Monitoring System may be determined according to the identified region/zone of interest. In some embodiments however, guidelines for the imaging system to focus on the identified region/zone(s) may be programmed after the design of the Ophthalmic Device.

At step 810, the Retinal Vascularization Monitoring System can monitor one or more pre-identified target points over pre-determined periods of time. Monitoring can include determining the cardiac rhythm from the rate of pulsations of a vessel over a particular period of time 815 and/or the displacement/changes of vessel(s) 820 over time. The monitoring may be triggered, for example, based on a timer function, blink actuation, or upon receiving a signal from a wireless device in communication with the Ophthalmic Device. In some embodiments, the wireless may serve as a user interface and may be a drug pump, smartphone, personal computer, tablet, and the such. Transmission of information with the wireless device can occur, for example, via a RF frequency, a local area network (LAN), and/or a private area network (PAN), depending on the communication device and functionality implemented by the Ophthalmic Device.

At steps 825 and 830, an audio/visual signal alert may be sent to the user when either the determined cardiac rhythm and/or determined rate of vascular displacement are outside a predetermined threshold. For example, a signal may be outputted when the system detects that the cardiac rhythm has increased/decreased to a hazardous level. The signal may be sent using a wireless device in communication with the Ophthalmic Device and/or through an audible signal using micro-acoustic elements included in the Ophthalmic Device. In some embodiments, the signal may be a visual signal using micro-photonic elements that may also be included in the Ophthalmic Device. The audible signal may be played in conjunction with a visual signal, e.g., as part of a video clip with safety instructions to reduce the risk of a fatal heart condition.

One or more of steps 835, 840, and 845 may occur depending on the particular embodiment implemented. Optionally at step 835, an actuation signal may be sent to a drug delivery apparatus to deliver a drug/active agent. The drug delivery mechanism may include, for example, a drug pump in wireless communication with the Ophthalmic Device. Optionally at step 640, the signal may be correlated with a specific event imputed by the patient using the wireless device as a user interface. For example, through a selection from a menu listing activities that can influence cardiac rhythm or blood pressure.

Also optionally, at step 845, the action and/or feedback from steps 810-840 can be recorded to improve future analysis, keep a medical record that can be accessed by an eye care practitioner, and/or tailor the Retinal Vascularization Monitoring System to the particular patient. In some embodiments, these recorded actions/records can also be sent/stored using the wireless device.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of monitoring the retinal vascularization of a patient's eye, the method comprising:
    identifying at least one location of a pulsating vessel in the retinal vascularization of an eye;
    providing an ophthalmic device configured to house a media insert containing a retinal vascularization monitoring system comprising an energy source in electrical connection and capable of energizing a micro-piezoelectric element with an electronic feedback circuit and a controller comprising a computer processor and a digital media storage device, wherein the media insert is configured for placement within a lens of the ophthalmic device;
    outputting a signal towards the at least one pulsating location;
    receiving, using the feedback circuit, a return signal from the outputted signal;
    imaging the at least one pulsating location using the change in the outputted signal and the return signal; and
    monitoring changes of the retinal vascularization by comparing said at least one identified portion images with a previous image of the same said at least one identified portion over time.

2. The method of claim 1, wherein the monitoring changes of the retinal vascularization include recording the changes in the diameter of the pulsating vessel over time.

3. The method of claim 2, additionally comprising:
    determining the cardiac rhythm of the patient using the recorded changes in the diameter of the pulsating vessel over time.

4. The method of claim 3, additionally comprising:
    generating a signal alert when the determined cardiac rhythm falls outside a pre-determined range.

5. The method of claim 4, wherein one or both the action of generating a signal alert to the patient and the determined cardiac rhythm is recorded as part of a patient's medical history.

6. The method of claim 1, wherein the monitoring changes of the retinal vascularization include looking at a rate of displacement of the pulsating vessel.

7. The method of claim 6, additionally comprising:
    sending a signal alert when the rate of displacement of the pulsating vessel a s outside a pre-determined range.

8. A method of monitoring the retinal vascularization of a patient's eye, the method comprising:
    identifying locations forming part of the retinal vascularization of the patient's eye including at least a portion of a pulsating vessel;
    providing an ophthalmic device configured to house a media insert containing retinal vascularization monitoring system comprising an energy source in electrical connection and capable of energizing a micro-piezoelectric element with an electronic feedback circuit and a controller comprising a computer processor and a digital media storage device, wherein the media insert is configured for placement within a lens of the ophthalmic device;
    detecting a change in a controlled the signal outputted towards the at least said portion of the pulsating vessel identified;
    imaging the at least said portion of the retinal vascularization of the patient's eye using the detected change in said controlled signal; and
    recording the changes in the at least said portion of the retinal vascularization between a series of images over time.

9. The method of claim 8, wherein the detecting the change in the controlled signal is performed at least in part by a feedback circuit.

10. The method of claim 8, further comprising transmitting, via a communication network, at least a portion of a return signal from the controlled signal.

11. The method of claim 8, further comprising sending at least one of an audio signal alert and a visual signal alert when at least one of a determined cardiac rhythm or a determined rate of vascular displacement are outside a predetermined threshold.

* * * * *